United States Patent [19]

Oku

[11] Patent Number: 5,554,893
[45] Date of Patent: Sep. 10, 1996

[54] SYSTEM FOR CONTROLLING SEMICONDUCTOR

[75] Inventor: Toshio Oku, Tokyo, Japan

[73] Assignee: Machida Endoscope Co., Ltd., Tokyo, Japan

[21] Appl. No.: 385,640

[22] Filed: Feb. 8, 1995

[30] Foreign Application Priority Data

Feb. 17, 1994 [JP] Japan .................................... 6-041743

[51] Int. Cl.⁶ .................................................... H01H 7/16
[52] U.S. Cl. ......................... 307/119; 307/112; 307/113; 439/489; 327/475; 327/545; 606/109; 606/117
[58] Field of Search ..................................... 307/119, 113, 307/112; 439/489; 128/6, 4; 327/545, 475

[56] References Cited

U.S. PATENT DOCUMENTS

| | | | |
|---|---|---|---|
| 4,863,233 | 9/1989 | Nieaber | 350/96.20 |
| 4,866,516 | 9/1989 | Hibino et al. | 358/98 |
| 4,869,237 | 9/1989 | Eino et al. | 128/6 |
| 4,920,413 | 4/1990 | Nakamura et al. | 358/98 |
| 5,228,560 | 7/1993 | Naslund | 200/275 |
| 5,435,748 | 7/1995 | Abe | 439/489 |

*Primary Examiner*—William M. Shoop, Jr.
*Attorney, Agent, or Firm*—Fish & Richardson P.C.

[57] ABSTRACT

A device that provides a control system which is capable of positively preventing a semiconductor from suffering from latch up. In order to prevent this latch up, a control circuit controls the semiconductor through a power source switch. The control circuit is capable of supplying a constant voltage to a power source terminal of the semiconductor when it is electrically connected to the power source circuit by turning on the power source switch, and thereafter supplying a control signal to a control terminal of the semiconductor. The control circuit is capable of stopping the output of the control signal to the control terminal and then stopping the supply of voltage to the power source terminal when disconnected from the power source circuit by turning off the power source.

3 Claims, 3 Drawing Sheets

SYSTEM FOR CONTROLLING SEMICONDUCTOR

BACKGROUND OF THE INVENTION

This invention relates to a system for controlling a semiconductor such as a CCD, and more particularly to an improvement of a construction for connecting an instrument having a semiconductor and a control unit to each other.

Taking, for example, an electronic endoscope system as disclosed in Japanese Laid-Open Patent Application No. Sho 59-70382, this system comprises an endoscope, a control unit connected to this endoscope, and a monitor television connected to this control unit. In operation, this endoscope is inserted into a patient's body and his/her body cavity is observed while watching the monitor television.

The endoscope includes a body, an insert portion extending from the body, a CCD (semiconductor) acting as an image pick-up element, which is mounted on a distal end of the insert portion, and a cable extending backwardly from the body. A first connector is mounted on a distal end of the cable. This first connector is connected to the CCD through electric wires passing through the cable, the body and the insertion portion.

The control unit contains therein a power source circuit for converting an AC voltage to a DC voltage, a control circuit which receives the DC voltage from the power source circuit, and a power source switch interposed between the power source circuit and the control circuit. The operating portion of the power source switch is mounted on a front wall of a housing of the control unit. A second connector is mounted on the front wall of the housing and connected to the control circuit.

The first connector of the endoscope is removably connected to the second connector of the control unit. By this, the control circuit and the CCD are connected to each other.

Incidentally, the CCD, like other semiconductors, has a possibility of suffering from a latch-up phenomenon. This latch-up occurs when a signal terminal is received in the state where no voltage is supplied to a power source terminal of the semiconductor. This results in breakage of the CCD.

In order to prevent this latch-up, the above-mentioned control circuit controls the semiconductor in the following manner. When the power source switch is turned on and the control circuit is connected to the power source circuit, the control circuit outputs a control signal to the signal terminal after it supplies the voltage to the power source terminal of the semiconductor. On the other hand, when the control circuit is disconnected from the power source circuit by turning off the power source switch, the supply of voltage to the power source terminal is stopped after the output of the control signal to the signal terminal has been stopped.

In the case where the first and second connectors are connected to each other in the OFF-state of the power source switch, and thereafter, the power source switch is turned on, the control circuit exhibits a latch-up preventive function. Therefore, a possible breakage of the CCD can be positively prevented. Also, in the case where the power source switch is turned off first and then the connecting state between the first and second connectors is removed, the control circuit exhibits the latch-up preventive function. Therefore, breakage of the CCD can be positively prevented.

However, in the case where the first and second connectors are connected to each other after the power source switch is turned on, the latch preventive function by the control circuit does not work any more. In addition, since the contact elements of the first and second connectors for transmitting control signals are often contacted immediately before the contact elements for supplying voltage to the power source terminal of the CCD are contacted to each other at the starting time of the connecting operation, the CCD receives the control signal before it receives the supply of voltage to the power source terminal. As a result, the CCD is broken by latch-up. Similarly, in the case where the connection between the first and second connectors is removed in the state where the power source switch is in the ON-state, there is still a possibility that the CCD is broken by latch-up.

In order to prevent the latch-up, it was a conventional practice to request the user to turn on the power source switch after the connector devices are connected and then remove the connection between the first connector and the second connector after the power source switch is turned off.

However, since this on/off operation of the power source switch and the sequential order of connection of the connectors are left to the user's manual operation, the CCD is frequently subjected to a failure by the user who inadvertently connects the connectors in wrong order.

SUMMARY OF THE INVENTION

The present system controls a semiconductor which comprises a first connector mounted on a cable, a second connector mounted on a front wall of a housing, a power source switch and a preventing means for preventing latch up from occurring in the system controlling the semiconductor.

One way latch up can be prevented is by having a connection ring mounted on an outer periphery of the first connector. After the contact elements of the first and second connector are connected to each other, the connection ring is threadedly engaged with the second connector. Once engaged the connection ring presses the operating portion for the power source switch to turn on the power source switch. By having the power source switch turned on after contact elements of the connectors are connected latch up is prevented.

Another way latch up is prevented is to have a flange formed on the outer periphery of the first connector.

The other features and advantages of the present invention will become apparent from the following explanation.

DETAILED DESCRIPTION OF THE EMBODIMENTS

Figure 1:
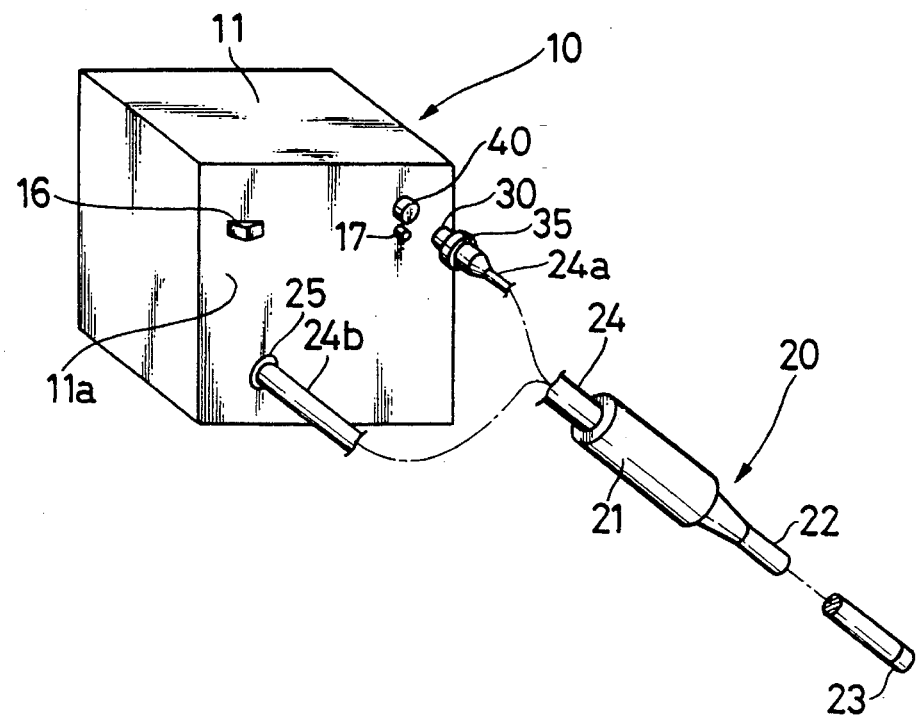
FIG. 1 is a perspective view showing a general construction of an electronic endoscope system according to the present invention.
Figure 2:
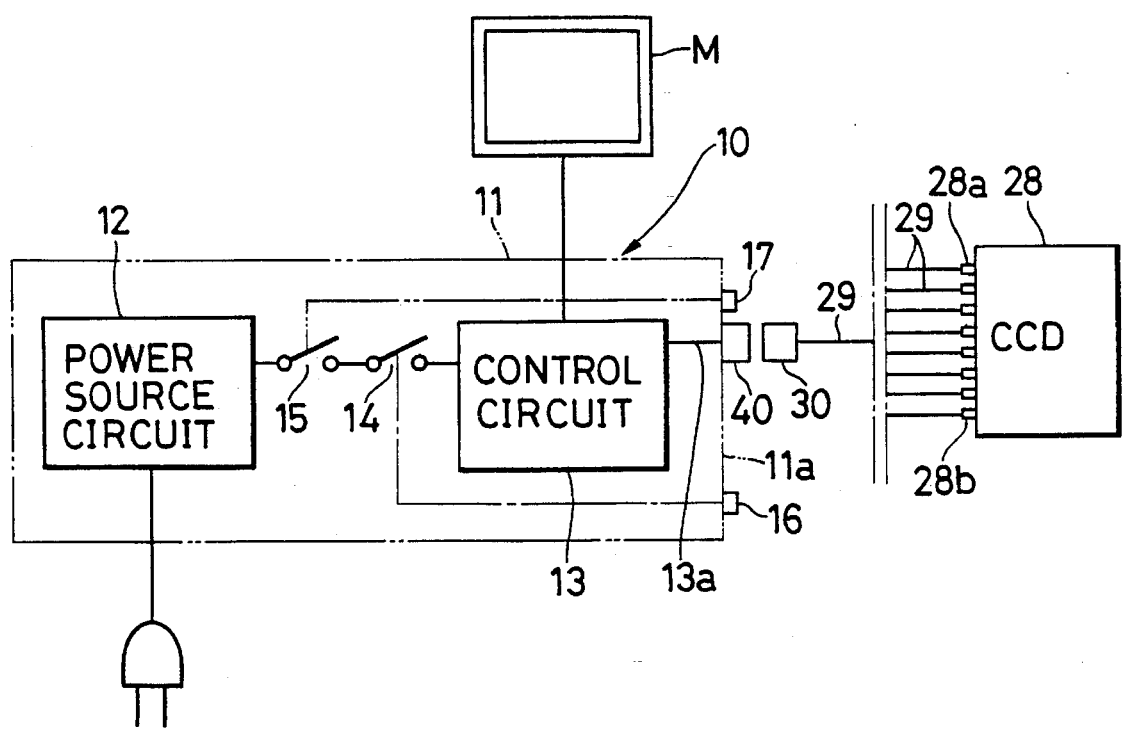
FIG. 2 is a circuit diagram of the electronic endoscope system.

One embodiment of a semiconductor control system according to the present invention, which is mounted on an electronic endoscope system, will be described with reference to FIGS. 1 to 3. As shown in FIGS. 1 and 2, the electronic endoscope system comprises a control unit 10, a monitor television M connected to the control unit 10, and an endoscope 20 removably connected to the control unit 10.

As shown in FIG. 1, the endoscope 20 includes a body 21, a flexible insert portion 22 extending from a distal end of the body 21, a tip 23 disposed on a distal end of the insert portion 22, a common cable 24 extending from a rear end of the body 21, and two branch cables 24a and 24b branched from the common cable 24. A distal end portion of the insert portion 22 can be bent by means of remote control using a control member (not shown) mounted on the body 21. A plug 30 (first connector) is mounted on a distal end of the branch cable 24a. An optical connector 25 is mounted also on the distal end of the other branch cable 24b.

The tip 23 is provided at distal end face thereof with an observation window and an illumination window. The illumination window and the optical connector 25 are optically connected to each other by a bundle of optical fibers (not shown). This bundle of optical fibers are allowed to pass through the insert portion 22, the body 21, the common cable 24, and the branch cable 24b. A light source device (not shown) is received in the housing 11 of the control unit 10. An illumination light from the light source device is irradiated through the illumination window after passing through the optical connector 25 and the optical fibers.

On the tip 23, there is provided a CCD 28 (semiconductor, see FIG. 2) acting as an image pick-up element, which is placed opposite to the observation window through an objective lens system. A power source terminal 28a and signal terminals 28b of this CCD 28, and a plurality of female-type contact elements, as later described, of the plug 30 are connected together by a plurality of signal lines 29 (several signal lines are grouped and indicated by a single line in FIG. 2). These signal lines 29 are allowed to pass through the insert portion 22, the body 21, the common cable 24 and the branch cable 24a.

Figure 3A:
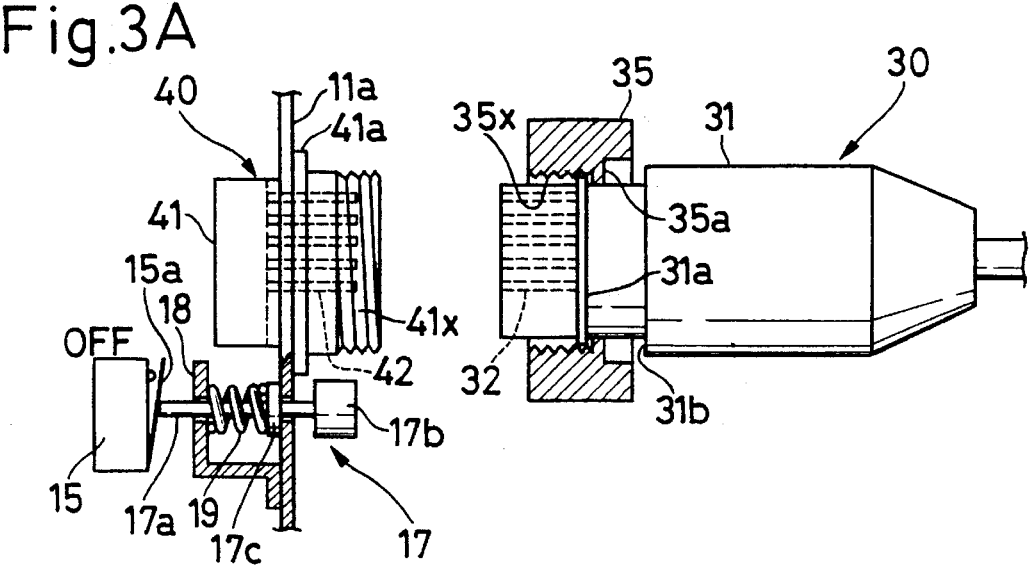
FIGS. 3(A) to 3(C) are sectional views sequentially showing various states of connectors and a power source switch which are used in the above system, in the order of the connecting processes.

The above plug 30 is conventionally known and has, as shown in FIG. 3A, a cylindrical body 31 and the plurality of female-type contact elements 32 supported by the body 31. The female contact elements 32 are received in a distal end portion of the body 31 and allowed to extend in parallel to the axis of the body 31, with its distal end facing an open end of the body 31.

A connection ring 35 (pressing member) is mounted on the plug 30 such that the ring can move in the axial direction and turn about the plug 30. An engagement flange 35a is formed on an intermediate portion of an inner periphery of the connection ring 35. The movable range of the connection ring 35 in the axial direction is determined by a front engagement position where the engagement flange 35a contacts an engagement flange 31a formed on the outer periphery of the body 31 and a rear engagement position where an engagement flange 35a contacts an annular step 31b formed on the outer periphery of the body 31.

A female-thread 35x is formed in the inner periphery of the connection ring 35 but at a location shifted forwardly from the engagement flange 35a.

The control unit 10 includes, within a housing 11, a power source circuit 12 for converting an AC voltage to a DC voltage, and a control circuit 13.

Two power source switches 14 and 15, which are mutually arranged in a serial relation, are interposed between the power source circuit 12 and the control circuit 13.

Operating portions 16 and 17 of the power source switches 14 and 15 and a receptacle 40 (second connector), which is connected to the control circuit 13 through a plurality of electric wires 13a (a single wire as a group of several wires is shown in FIG. 2), are mounted on the front wall 11a of the housing 11.

The receptacle 40 is known. As shown in FIG. 3A, the receptacle 40 comprises a cylindrical body 41, a plurality of pin-like male-type contact elements 42 supported within the body 41. Each contact element 42 is allowed to extend in parallel with the axis of the body 41 and surrounded by the body 41, with its distal end facing the open end of the body 41. The body 41 is allowed to extend through the front wall 11a such that its axis extends perpendicular to the front wall 11a of the housing 11. A flange 41a is formed on the outer periphery of the body 41. By fixing this flange 41a to the front wall 11a, the body 41 is fixed to the front wall 11a. A male-thread 41x is formed on the outer periphery of the distal end of the body 41. The previously mentioned female-thread 35x of the connection ring 35 is threadedly engaged with the male-thread 41x of this receptacle 40.

As shown in FIG. 2, the operating portion 16 of the power source switch 14 is of a see-saw type and mounted on the front wall 11a of the housing 11 but situated away from the receptacle 40 as in the case with the conventional device. As shown in FIGS. 1 to 3, the operating portion 17 of the other power source switch 15 protects from the front wall 11a in the vicinity of the receptacle 40. In this embodiment, although the operating portion 17 is arranged below the receptacle 40, FIG. 2 does not show a correct positional arrangement. It should be noted that this operating portion 17 may of course be situated above, right or left of the receptacle 40.

As shown in FIG. 3A, the operating portion 17 of the power source switch 15 includes a shaft 17a, a button portion 17b disposed at an external end of the shaft 17a, and a spring retainer portion 17c disposed at an intermediate portion of the shaft 17a. The shaft 17a is allowed to extend through the front wall 11a, and a bracket 18 secured to the front wall 11a. Between this bracket 18 and the spring retainer portion 17c, a compressed coil spring 19 is interposed such that the spring 19 is wound on the shaft 17a. The shaft 17 is biased outwardly by the resiliency of the coil spring 19 and the spring retainer portion 17c is in contact with the front wall 11a. In that state, the button portion 17b is away from the front wall 11a and located forwardly of the front wall 11a. Although an inner end of the shaft 17a is in contact with a contact element 15a of the power source switch 15 having the form of a micro-switch, the power source switch 15 is in the OFF-state.

With the above construction, the CCD 28 of the endoscope 20 is connected to the control circuit 13 within the control unit 10 by inserting the plug 30 into the receptacle 40. More specifically, as shown in FIG. 3A, the operator holds the plug 30 such that the plug 30 coaxially faces the receptacle 40. Then, by moving the plug 30 toward the receptacle 40, the body 31 of the plug 30 is inserted into the body 41 of the receptacle 40. Further movement of the plug 30 in the mentioned direction causes the contact elements 32 of the plug 30 to mutually fit for electric connection to the contact elements 42 of the receptacle 40 as shown in FIG. 3B.

When the plug 30 is inserted, the distal end of the female-thread 35x of the connection ring 35 contacts the distal end of the male-thread 41x of the receptacle 40 and therefore, the connection ring 35 is prevented from further movement. As a result, the ring 35 is retreated relative to the plug 30. The plug 30 is stopped by the step 31b being contacted with the engagement flange 35a of the connection ring 35. When the plug 30 is in its stop position, the contact elements 32 of the plug 30 are all positively connected to all contact elements 42 of the receptacle 40 over a predetermined length. It should be noted that the plug 30 may be stopped by other suitable means. For example, it may be designed such that before the step 31b contacts the flange 35a, the distal end of the body 31 of the plug 30 contacts a stopper formed inside the receptacle 40.

Figure 3B:
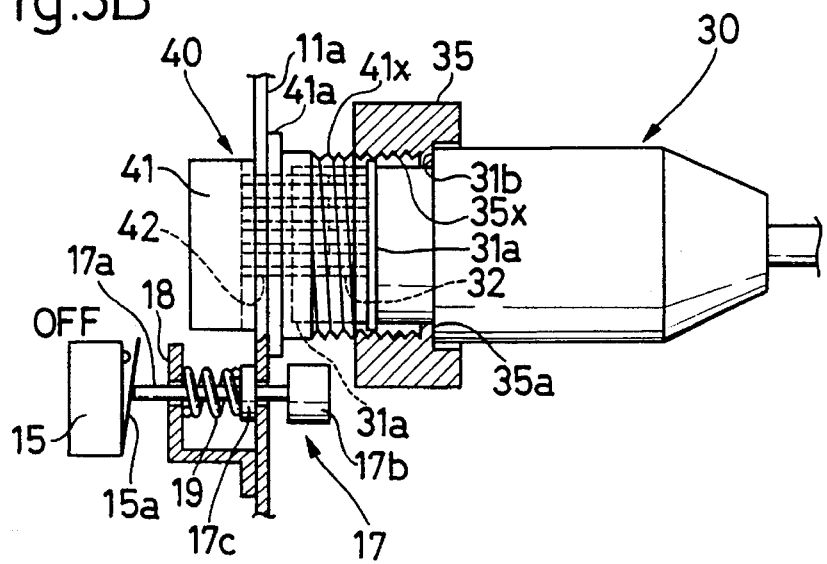

In FIG. 3B, special attention should be paid to the fact that when the distal end of the connection ring 35 is in contact with the distal end of the receptacle 40, the connection ring 35 is away from the button portion 17b of the operating portion 17 of the power source switch 15 and therefore, the power source switch 15 is maintained in the OFF-state. Accordingly, in this OFF-state of the power source switch 15, the contact elements 32 of the plug 30 and the contact elements 42 of the receptacle 40 are fully connected to each other.

Figure 3C:
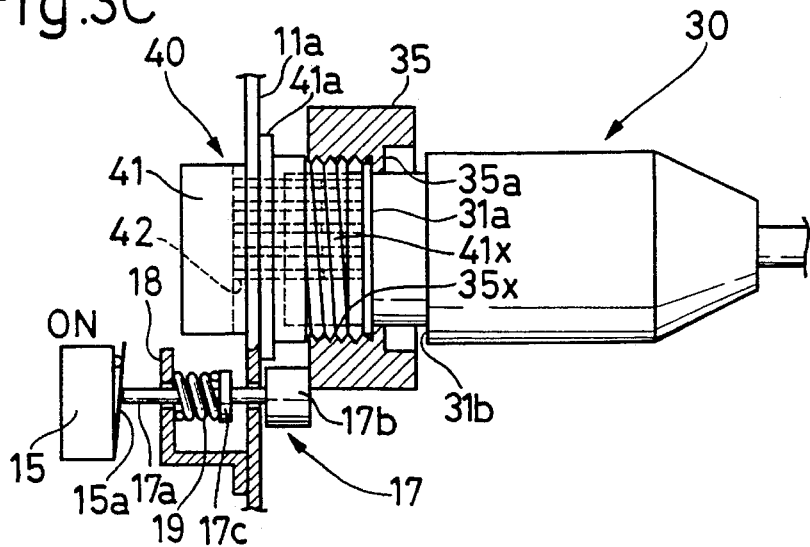

Next, as shown in FIG. 3C, the connection ring 35 is turned so that the female-thread 35x is threadedly engaged with the male-thread 41x of the receptacle 40. By doing this, the plug 30 and the receptacle 40 are firmly connected together (i.e., connection is completed).

When the connection ring 35 is brought into engagement with the receptacle 40, the connection ring 35 is moved in the axial direction and pushes the button portion 17b of the operating portion 17 of the power source switch 15 with its distal end face. Therefore, the shaft 17a of the operating portion 17 is retreated to push the contact element 15a of the power source switch 15 with its inner end, so that the power source switch 15 is turned on. This turning-on operation of the power source switch 15 is performed before the completion of the threaded-engagement by the connection ring 35.

Next, the operating portion 16 of the power source switch 14 is operated to turn on the power source switch 14. As a result, the DC voltage from the power source circuit 12 is supplied to the control circuit 13. In response to this, the control circuit 13 starts controlling the CCD 28. In the control circuit 13, a constant voltage is supplied to the power source terminal 28a of the CCD 28 first and then, a control signal is output to the signal terminals 28b. What is important here is that at the time when the control circuit 13 starts its controlling operation, connection between the connectors 30 and 40 are completed, and the control circuit 13 and the CCD 38 are already electrically connected to each other. As a result, the supply of constant voltage and the output of control signal are performed in given order by the control circuit 13 and therefore, latch-up can be positively prevented and thus, breakage of the CCD 28 can be prevented.

Next, for removing the endoscope 20 from the control unit 10, the connection ring 35 is likewise turned but in the reverse way so as to be retreated. As this connection ring 35 is retreated, the operating portion 17 is projected by the force of the coil spring 19 and the power source switch 15 is turned off. By this, the control circuit 13 finishes its controlling operation with respect to the CCD 28. At the time of finish of the controlling operation, since the control circuit 13 stops supplying the constant voltage to the power source terminals 28a of the CCD 28 after the output of the control signal to the CCD 28 is stopped, latch-up of the CCD 28 can be prevented. At that time, since the connection between the plug 30 and the receptacle 40 is maintained, the latch-up preventing operation is assuredly performed. By further loosening the engagement of the connection ring 35 so as to further retreat the connection ring 35 after the power source switch 15 is turned off, the connection ring 35 is removed from the receptacle 40. Then, the plug 30 is pulled out of the receptacle 40 to remove the connection between the contact elements 32 and 42. At the time of the removal of connection, since the controlling operation with respect to the CCD 28 is already finished, the removal of connection does not affect adversely to the CCD 28.

The user is requested to turn off the other power source switch 14 before removing the connection between the plug 30 and the receptacle 40. Even if the user should forget this turning-off operation, the latch-up prevention is ensured because the power source switch 15 is already in the Off-position when the connection is to be removed.

In the above embodiment, the connection ring may be connected to the receptacle by other suitable means than the thread means. For example, it may be designed such that a pin is formed on the outer periphery of the cylindrical portion of the receptacle and an engagement groove is formed in the connection ring. This engagement groove has a first portion extending in the axial direction from the distal end of the connection ring, and a second portion extending in a circumferential direction from a rear end of this first portion. The engagement groove is generally of an L-shape. A mounting structure of the connection ring to the plug is the same as the preceding embodiment. In this embodiment, after the electrical connection between the contact elements of the plug and the contact elements of the receptacle is finished, the connection ring is moved in the axial direction with the pin inserted in the first portion of the engagement groove, and then the connection ring is turned to bring the pin to the second portion of the engagement groove to connect the connection ring and the receptacle together, and therefore to connect the receptacle and the plug together. In the midway of the movement of the connection ring in the axial direction with the pin positioned in the first portion of the engagement groove as mentioned above, the connection ring pushes the operating portion of the power source switch to turn on the power source switch.

Figure 4:
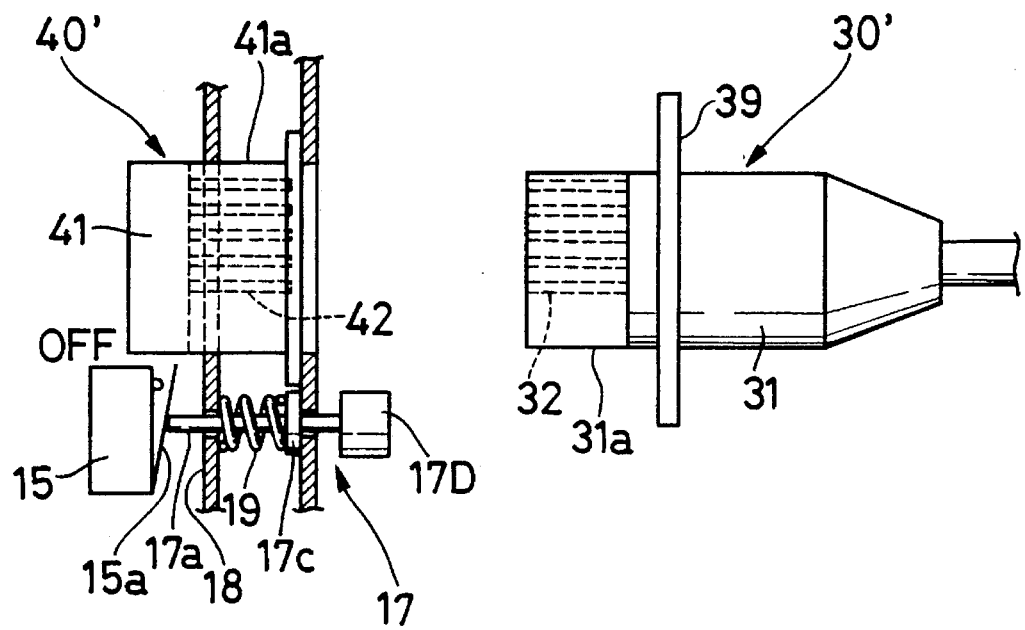
FIG. 4 is a sectional view showing connectors and a power source switch according to a modified embodiment.

FIG. 4 shows a modified embodiment of a plug 30' and a receptacle 40'. In FIG. 4, like parts of the preceding embodiment are denoted by like reference numerals, respectively and description thereof is omitted. In this embodiment, the plug 30' is simply inserted into the receptacle 40'. A pressing flange (pressing member) 39 is formed on the outer periphery of the body 31 of the plug 30'. During the process of insertion of the plug 30' into the receptacle 40', the pressing flange 39 pushes the operating portion 17 of the power source switch 15 to turn on the power source switch 15. What is important here is that the forming position of the pressing flange 39 on the body 31 is determined such that after the electrical connection between all contact elements 32 of the plug 30' and all contact elements 42 of the receptacle 40 is finished, the power source switch 15 is turned on.

As shown in FIG. 4, in the case where the connectors are connected to each other simply by insertion, it may be designed such that the diameter of the cylindrical portion of the first connector on the side of the CCD is made larger than the diameter of the cylindrical portion of the second connector on the side of the control unit, so that the contact elements of them are electrically connected to each other with the cylindrical portion of the second connector received in the cylindrical portion of the first connector. In that case, the distal end face of the cylindrical portion of the first connector may be served as a pressing portion for pushing the operating portion of the power source switch.

Figure 5:
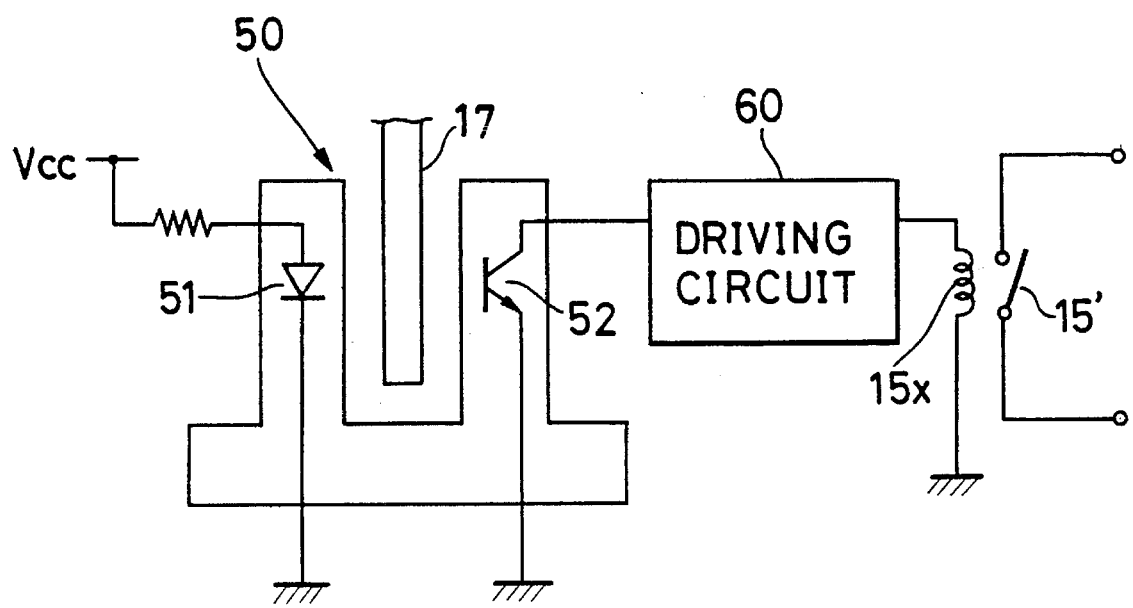
FIG. 5 is a circuit diagram of a power source switch according to a modified embodiment.

In FIG. 5, a power source switch 15' comprises a relay switch. The power source switch 15' is connected to a photo-coupler 50. This photo-coupler 50 comprises a photodiode 51 and a photo-transistor 52. The previously mentioned shaft 17*a* of the operating portion 17 can be moved in and out of between the photodiode 51 and the photo-transistor 52. Normally, since the shaft 17*a* is biased by the coil spring, it is not located between the photodiode 51 and the photo-transistor 52. In that case, the photo-transistor 52 is turned on upon receipt of light from the photodiode 51 and a driving circuit 60 is opened so that the coil 15*x* is not excited. When the shaft 17*a* is retreated pushed by the connection ring 35 or the pressing flange 39, the shaft 17*a* enters between the photodiode 51 and the photo-transistor 52. As a result, since the photo-transistor 52 is turned off, the driving circuit 60 is closed to excite the coil 15*x*. As a result, the power source switch 15' is turned on.

It is acceptable that the micro-switch 15 of FIG. 3 is used as the power source switch and its contact element 15*a* is served directly as the operating portion. In that case, the power source switch 15 is mounted on the front surface of the front wall 11*a*, and the contact element 15*a* is pushed by the pressing member directly mounted on the second connector.

It is also acceptable that a pin is disposed, as the pressing member, on the connector of the endoscope, and this pin is allowed to extend through a through-hole formed in the front wall, so that the pin pushes a contact element of a power source switch disposed within the control unit.

In the above embodiments, the power source switch 14, which can be turned on/off by means of operation of the user, may be omitted.

The present invention may be applied to a control system equipped with an image pick-up instrument having a CCD mounted on a distal end of a hard tube, instead of an endoscope. Also, the present invention may be applied to a system for controlling semiconductors other than CCD.

What is claimed is:

1. A semiconductor control system comprising:
  (a) an instrument including a semiconductor;
  (b) a cable extending from said instrument;
  (c) a first connector mounted on one end of said cable and electrically connected to said semiconductor; and
  (d) a control unit including:
    (i) a housing;
    (ii) a second connector disposed on a front wall of said housing, said first connector being removably connected to said second connector;
    (iii) a power source circuit received in said housing;
    (iv) a control circuit received in said housing and connected to said second connector; said control circuit being further connected to said power source circuit through a power source switch, said control circuit being capable of supplying a constant voltage to a power source terminal of said semiconductor when electrically connected to said power source circuit by turning on said power source switch, and thereafter supplying a control signal to a control terminal of said semiconductor, said control circuit being capable of stopping the output of control signal to said control terminal and then stopping the supply of voltage to said power source terminal when disconnected from said power source circuit by turning off said power source;
    (v) characterized in that said housing is provided on a front wall thereof in the vicinity of said second connector with an operating portion for said power source switch, said operating portion being movable between a first position and a second position situated backwardly of said first position and in a direction generally perpendicular to said front wall of said housing, said power source switch being in an Off-state when said operating portion is in said first position, said power source switch being turned on in a midway of the movement of said operating portion from said first position to said second position, said first connector being provided with a pressing member, said pressing member, when said first connector is connected to said second connector, being moved toward said front wall of said housing, at that time, said pressing member pushing said operating portion so that said operating portion is moved from said first position to said second position; and
  (e) said control unit including a second power source switch disposed between said power source circuit and said control unit and in a serial relation with the first-mentioned power source switch, a second operating portion for turning on/off said second power source switch being provided on said front wall of said housing but away from said second connector.

2. A semiconductor control system comprising:
  (a) an instrument including a semiconductor;
  (b) a cable extending from said instrument;
  (c) a first connector mounted on one end of said cable and electrically connected to said semiconductor, said first connector having a cylindrical first body and a plurality of first contact elements disposed within said first body;
  (d) a control unit including:
    (i) a housing;
    (ii) a second connector disposed on a front wall of said housing, said first connector being removably connected to said second connector, said second connector having a cylindrical second body and a plurality of second contact elements disposed within said second body;
    (iii) a power source circuit received in said housing;
    (iv) a control circuit received in said housing and connected to said second connector;
    (v) a power source switch through which said control circuit is further connected to said power source circuit, an operating portion for said power source switch being mounted on said front wall of said housing in the vicinity of said second connector, said operating portion being maintained in a first position projected from said front wall of said housing under the effect of a spring disposed on a back side of said front wall of said housing, said operating portion being movable backwardly to a second position, said power source switch being in an off-state when said operating portion is in said first position, and said power source switch being turned on in a midway of the backward movement of said operating portion from said first position to said second position; and
  (e) a connection ring mounted on an outer periphery of said first body of said first connector, said connection ring being turnable about said first body and movable in an axial direction of said first body within a predetermined range, said connection ring being threadedly engaged with said second body of said second connector after said first and second contact elements being connected to each other, said connection ring pressing said operating portion for said power source switch in the course of the engagement of said connection ring with said second body, thereby said operating portion being moved backwardly to turn on said power source switch.

3. A semiconductor control system comprising:

(a) an instrument including a semiconductor;

(b) a cable extending from said instrument;

(c) a first connector mounted on one end of said cable and electrically connected to said semiconductor, said first connector having a cylindrical first body and a plurality of first contact elements disposed within said first body;

(d) a control unit including:

(i) a housing;

(ii) a second connector disposed on a front wall of said housing, said first connector being removably connected to said second connector, said second connector having a cylindrical second body and a plurality of second contact elements disposed within said second body;

(iii) a control circuit received in said housing;

(iv) a control circuit received in said housing and connected to said second connector;

(v) a power source switch through which said control circuit is further connected to said power source circuit, an operating portion for said power source switch being mounted on said front wall of said housing in the vicinity of said second connector, said operating portion being maintained in a first position projected from said front wall of said housing under the effect of a spring disposed on a back side of said front wall of said housing, said operating portion being movable backwardly to a second position, said power source switch being in an off-state when said operating portion is in said first position, and said power source switch being turned on in a midway of the backward movement of said operating portion from said first position to said second position; and (e) a flange formed on an outer periphery of said first body of said first connector, said first and second contact elements being connected to each other by moving said first connector toward said second connector, said flange being moved together with said first connector to press and backwardly move said operating portion for said power source switch, said power source switch being turned on after said first and second contact elements are connected.

* * * * *